United States Patent
Stibich et al.

(10) Patent No.: US 11,547,772 B2
(45) Date of Patent: *Jan. 10, 2023

(54) PRE-DOFFING DISINFECTION SYSTEMS AND METHODS

(71) Applicant: Xenex Disinfection Services INC., San Antonio, TX (US)

(72) Inventors: Mark A. Stibich, Santa Fe, NM (US); Sarah E. Simmons, San Antonio, TX (US); Edward C. Guerrero, Jr., San Antonio, TX (US); Paul P. Froutan, Katy, TX (US)

(73) Assignee: Xenex Disinfection Services Inc., San Antonio, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/112,213

(22) Filed: Dec. 4, 2020

(65) Prior Publication Data

US 2021/0113728 A1    Apr. 22, 2021

Related U.S. Application Data

(60) Division of application No. 16/506,322, filed on Jul. 9, 2019, now Pat. No. 10,874,760, which is a division
(Continued)

(51) Int. Cl.
*A61L 2/10* (2006.01)
*A61L 2/24* (2006.01)
*A61L 2/26* (2006.01)

(52) U.S. Cl.
CPC ............ *A61L 2/24* (2013.01); *A61L 2/10* (2013.01); *A61L 2/26* (2013.01); *A61L 2202/11* (2013.01);
(Continued)

(58) Field of Classification Search
CPC .......... A61L 2/108; A61L 2/081; A61L 2/082; A61L 2/10; A61L 2/12; A61L 2202/25; A61L 2202/26
See application file for complete search history.

(56) References Cited

U.S. PATENT DOCUMENTS 2,821,982 A    2/1958  Lyburn
4,952,369 A  *  8/1990  Belilos .................. A61L 2/10
                                                    422/24
(Continued)

OTHER PUBLICATIONS

European Patent Office, Office Action for European Patent Application No. 15 785 031.4 dated Oct. 20, 2021, 5 pages.

*Primary Examiner* — Eliza W Osenbaugh-Stewart
(74) *Attorney, Agent, or Firm* — Egan, Enders & Huston LLP.

(57) ABSTRACT

Methods and systems are provided which project germicidal light from a lamp toward an individual donned in outerwear to disinfect the outerwear. In specific embodiments, germicidal light is projected toward an individual situated greater than approximately 1 foot from the light source. Some systems include sensor/s for detecting presence of an individual within a target area a set distance from the disinfection apparatus comprising the light source and program instructions for commencing operation of the disinfection apparatus based on information from the sensor/s. In addition or alternatively, some systems include reflective panel/s exhibiting greater than approximately 85% reflectance. In such cases, the systems may include program instructions for determining operating parameters of the disinfection apparatus and/or positions of the reflective panel/s based on information regarding an individual who is in the presence of the disinfection apparatus or who is scheduled to be in the presence of the disinfection apparatus.

18 Claims, 3 Drawing Sheets

Related U.S. Application Data of application No. 15/486,373, filed on Apr. 13, 2017, now Pat. No. 10,391,189, which is a continuation of application No. PCT/US2015/055784, filed on Oct. 15, 2015.

(60) Provisional application No. 62/064,071, filed on Oct. 15, 2014.

(52) U.S. Cl.
CPC ..... *A61L 2202/122* (2013.01); *A61L 2202/14* (2013.01); *A61L 2202/26* (2013.01)

(56) References Cited

U.S. PATENT DOCUMENTS

| | | | |
|---|---|---|---|
| 6,692,694 B1 * | 2/2004 | Curry | A61L 2/186 422/74 |
| 9,440,041 B1 | 9/2016 | Lacayo | |
| 10,391,189 B2 * | 8/2019 | Stibich | A61L 2/084 |
| 2004/0030371 A1 | 2/2004 | Barghelama | |
| 2012/0313532 A1 | 12/2012 | Stibich et al. | |

* cited by examiner

PRE-DOFFING DISINFECTION SYSTEMS AND METHODS

PRIORITY CLAIM

This application is a divisional of U.S. patent application Ser. No. 16/506,322 filed Jul. 9, 2019, which is a divisional of U.S. patent application Ser. No. 15/486,373 filed Apr. 13, 2017, now U.S. Pat. No. 10,391,189 which is a continuation of International Patent Application No. PCT/US2015/055784 filed Oct. 15, 2015, which designates the United States and claims priority to U.S. Provisional Patent Application No. 62/064,071, filed Oct. 15, 2014.

BACKGROUND OF THE INVENTION

1. Field of the Invention

This invention generally relates to disinfection systems and methods and, more specifically to, disinfection systems and methods for pre-doffing applications.

2. Description of the Related Art

The following descriptions and examples are not admitted to be prior art by virtue of their inclusion within this section.

Currently, healthcare workers (HCWs) must don personal protective equipment (PPE) to provide care to infectious or potentially infectious individuals or to clean areas occupied or previously occupied by infectious or potentially infectious individuals. The infectious individuals generally include patients diagnosed with a specific pathogen, such as the Ebola virus. The potentially infectious individuals generally include patients suspected of having been infected with a particular pathogen (e.g., some of these patients may be awaiting diagnostic testing regarding the particular pathogen). The purpose of PPE is to keep bodily fluids, patient contact, airborne pathogens and/or contact with surfaces in the patient care environment from infecting HCWs. PPE is generally needed for any activities that may put a HCW into contact with an infected patient, a potentially infectious patient and/or potentially contaminated environments and equipment, such as but not limited to the delivery of food and medication, medical procedures, patient examinations and the cleaning of patient environments.

The doffing, or removal, of PPE is a complex process that requires training and practice. When PPE is removed, the HCW must take special care to assure that his or her hands or other parts of the body do not come into contact with the exterior surfaces of the PPE. This is especially difficult as PPE must often be turned inside out and disposed of during the doffing process. Many protocols insist that a second person, also in PPE observe the doffing process and be certain that protocols are followed. In many circumstances, HCWs do not have experience with PPE and there is a risk of an error in the doffing process that could lead to the infection of an HCW. There have been documented cases of Ebola transmission due to errors occurring during the doffing process, for example.

In some cases, the exterior of PPE is sprayed with a liquid disinfectant (such as a chlorine based solution) to provide extra assurance during the doffing process. This is often done in facilities dedicated to the care of highly infective patients and/or laboratories conducting diagnostic or experimental testing of particular infectious pathogens. Spraying with liquid disinfectants, however, is not specified in many protocols, such as many acute care hospital PPE guidelines. As such, standard hospitals often do not have the capacity to spray HCWs each time they doff PPE due to issues in creating infrastructure where the liquid disinfectant can drain and can be contained if a drain is blocked. Additionally, spraying is only appropriate when the PPE is waterproof, chemical resistant and there is no exposed skin. In particular, some PPE may absorb or disintegrate by contact with liquid disinfectants, damaging the integrity of the PPE and potentially exposing areas of the HCW to the liquid disinfectant and/or to pathogens transmitted from the exterior of the PPE. Furthermore, some types of PPE leave areas of skin exposed. In such cases, the liquid disinfectant could undesirably contact the exposed skin. Moreover, spraying PPE with a liquid disinfectant could pose an inhalation risk to the HCW.

Accordingly, it would be beneficial to develop alternative methods and systems which decrease the pathogenic contamination levels of PPE prior to doffing PPE.

SUMMARY OF THE INVENTION

The following description of various embodiments of apparatuses is not to be construed in any way as limiting the subject matter of the appended claims.

Systems and methods are provided which disinfect PPE or other types of outerwear and/or clothing with germicidal light while it is worn by an individual.

Embodiments of a method include generating ultraviolet electromagnetic radiation subtype C (UVC) light via an ultraviolet light source and projecting the UVC light toward an individual situated greater than approximately 1 foot from the ultraviolet light source.

Other embodiments of a method include generating germicidal light via a lamp and projecting the germicidal light toward an individual, wherein the individual is donned in clothing and/or personal protective equipment such that no skin of the individual is exposed to the lamp.

Embodiments of systems include a disinfection apparatus having one or more UVC light sources, wherein the disinfection apparatus is configured such that when the disinfection apparatus is arranged and operational in a room UVC light generated from the one or more UVC light sources is emitted to a region between approximately 2 feet and approximately 4 feet from a floor of the room. The system further includes one or more sensors for detecting presence of an individual within a target area a set distance from the disinfection apparatus. Furthermore, the system includes a storage medium comprising program instructions which are executable by a processor for commencing operation of the disinfection apparatus to generate and project UVC light exterior to the disinfection apparatus upon the one or more sensors detecting presence of an individual in the target area.

Other embodiments of systems include a disinfection apparatus having one or more germicidal light sources. The systems further include one or more reflective panels exhibiting greater than approximately 85% reflectance and a storage medium comprising program instructions executable by a processor for determining operating parameters of the disinfection apparatus and/or positions of the one or more moveable reflective panels based on information regarding an individual who is in the presence of the disinfection apparatus or who is scheduled to be in the presence of the disinfection apparatus.

BRIEF DESCRIPTION OF THE DRAWINGS

Other objects and advantages of the invention will become apparent upon reading the following detailed description and upon reference to the accompanying drawings in which.

Figure 1:
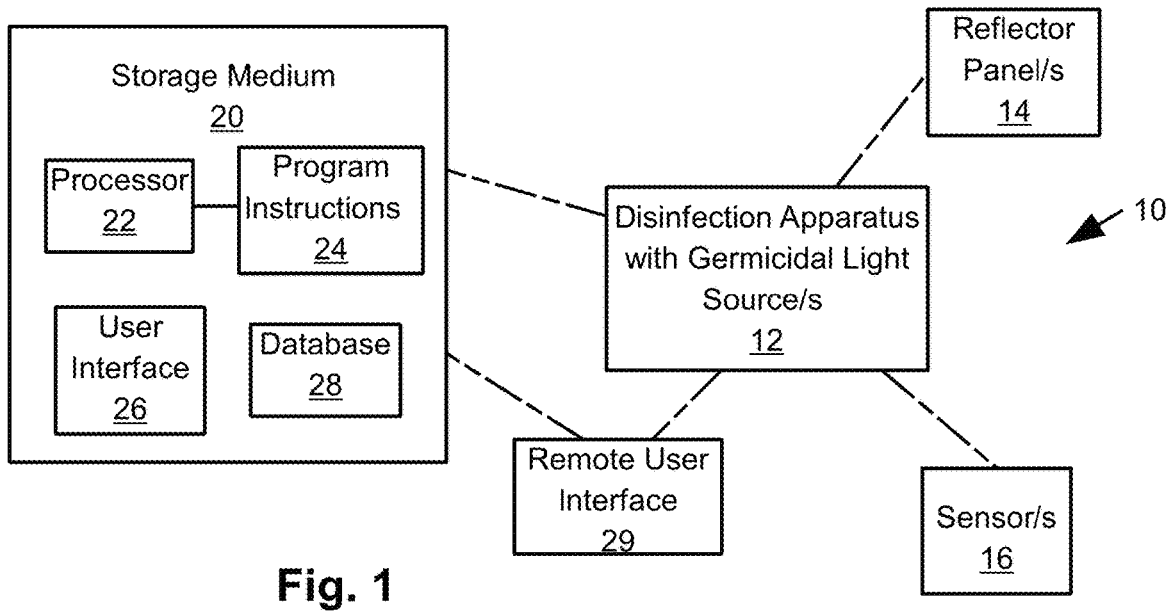
FIG. 1 illustrates a schematic diagram of an example system for performing a pre-doffing disinfection process.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

Systems and methods are provided which disinfect personal protective equipment (PPE) or other types of outerwear and/or clothing with germicidal light while it is worn by an individual. The systems and methods reduce the risk of an individual being infected by pathogens. In general, the individual may be any person which, while wearing the PPE or other types of outerwear and/or clothing, provided care to an infectious or potentially infectious individual, came into contact or was in the same room/environment with an infectious or potentially infectious individual, and/or cleaned an environment in which an infectious or potentially infectious individual resided. Examples of individuals include but are not limited to doctors, nurses and housekeeping personnel, all of which may be referred to herein as healthcare workers (HCWs). The methods and systems described herein may also be employed on non-HCWs, such as but not limited to family members and friends, emergency responders, and administrative personnel of a healthcare facility. In any case, the systems and methods may be employed prior to a doffing process to remove the PPE, outerwear or clothing and, thus, the systems and methods described herein may be referred to as pre-doffing methods and systems.

In general, the PPE, outerwear and/or clothing worn by an individual for the methods described herein may include any wear of an individual that has come into contact or was in the same room/environment with an infectious or potentially infectious individual. The term "clothing" as used herein refers to any covering that an individual may wear to cover at least a portion of their body. Examples of clothing include but are not limited to pants, shirts, coats, gloves, shoes, and hats. The term "outerwear" as used herein refers to any covering that an individual may over another piece of clothing, such as a coat. The term "PPE" as used herein refers to devices, equipment, gear, outerwear and/or clothing specifically designed to protect an individual's body from a hazard. The hazard may be physical, electrical, heat, chemicals, biohazards, airborne particulate matter or any combination thereof. Examples of PPE include but are not limited to gloves, eye protection, shoes, shoe covers, caps, hoods, face masks, respirators, coveralls, vests, gowns and/or full body suits. PPE worn by an individual for the methods described herein may vary depending on protocols, particularly for given pathogens and/or regarding governing bodies imparting such protocols. Non-PPE types of outerwear and/or clothing which may be worn by an individual for the methods described herein may include any wear that a HCW may wear during activities of taking care of a patient or wear that may be worn by a non-HCW, such as but not limited to scrubs, lab coats, uniforms, shoes, and ordinary clothing.

As set forth in more detail below, it may be important in some embodiments for an individual to be donned with clothing and/or PPE such that no skin is exposed to the lamp generating the germicidal light used to disinfect the clothing and/or PPE. In particular, some of the methods and systems described herein may generate and project ultraviolet (UV) light toward the individual. UV light is a known health hazard to eyes and skin and, thus, it may be prudent (as a safety precaution) or it may be required (due to exposure regulations) for an individual to be donned with clothing and/or PPE such that no skin is exposed to a lamp generating UV light during the disinfection process. In some cases, an individual may be donned in PPE with no skin exposure due to the protocol required for the activity performed by the individual who comes into contact or was in the same room/environment with an infectious or potentially infectious individual. In other cases, an individual may be donned in PPE and/or clothing which does not cover the entire body. In such cases, it may be desirable for the individual to put on additional clothing and/or PPE such that there is no skin exposure for the disinfection process.

As set forth below, eye protection and face mask PPE used for the methods described herein are preferably configured to block germicidal light, particularly UV light and more particularly UVC light. As a further precaution, the methods described herein may have the individual keep his/her eyes closed during the disinfection process to minimize the risk of exposure to the face and eyes. In yet other cases, an individual may not need to have all skin covered during the disinfection process. In particular, and as further set forth below, the germicidal light considered for the methods and systems described herein may include ultraviolet light and/or high-intensity narrow-spectrum (HINS) light. In cases in which the germicidal lamp does not generate UV light over set exposure limits (e.g., the criteria of occupational exposure to ultraviolet radiation recommended by the Center for Disease Prevention and Control) or does not generate UV light at all (i.e., generates only HINS light), full skin coverage of the individual may not be necessary for the disinfection process.

The terms "germicidal light source" and "germicidal lamp" are used interchangeably herein and refer to a collection of one or more components used to generate and disperse germicidal light. The term "germicidal light" refers to light which is capable of deactivating or killing microorganisms, particularly disease carrying and/or disease producing microorganisms (a.k.a., germs). The term "germicide" as used herein refers to an agent for deactivating or killing microorganisms, particularly disease carrying and/or disease producing microorganisms (a.k.a., germs). The term "kill," as used herein, means to cause the death of an organism. The term "deactivate," as used herein, means to render an organism unable to reproduce without killing. As such, a germicide which is configured to deactivate a microorganism refers to an agent which renders a microorganism unable to reproduce but leaves the organism alive.

Ranges of light which are known to be germicidal include ultraviolet light between approximately 200 nm and approximately 320 nm, particularly 205 nm, 230 nm and between 260 nm and 265 nm, and visible violet-blue light (also known as high-intensity narrow-spectrum (HINS) light) between approximately 400 nm and approximately 470 nm, particularly 405 nm. As used herein, UVA light is ultraviolet electromagnetic radiation subtype A with a wavelength between 320 nm to 400 nm, UVB light is ultraviolet electromagnetic radiation subtype B with a wavelength between 280 nm to 320 nm, and UVC light is ultraviolet electromagnetic radiation subtype C (UVC) with a wavelength between 200 nm to 280 nm. In some cases, the germicidal light sources considered for the methods and systems described herein may be polychromatic in that they generate light of more than one wavelength. In some embodiments, a germicidal light source may generate ranges of light which are not germicidal such as but not limited to visible light greater than approximately 500 nm, but such capability will not deter from the reference of the light sources being germicidal. Furthermore, a light source or lamp may, in some cases, be characterized in the type of light it generates, but such characterization need not limit the light source or lamp to generating only that type of light. For example, an ultraviolet lamp is one which generates ultraviolet light but it may produce light of other wavelengths. In any case, the germicidal light sources considered for the disinfection apparatuses may be of any size and shape, depending on the design specifications of the apparatuses.

Examples of germicidal light sources which may be configured to generate ultraviolet light and/or high-intensity narrow-spectrum (HINS) light include discharge lamps, light emitting diode (LED) solid state devices, and excimer lasers. HINS lamps are generally constructed of LEDs. A discharge lamp as used herein refers to a lamp that generates light by means of an internal electrical discharge between electrodes in a gas. The term encompasses gas-discharge lamps, which generate light by sending an electrical discharge through an ionized gas (i.e., a plasma). The term also encompasses surface-discharge lamps, which generate light by sending an electrical discharge along a surface of a dielectric substrate in the presence of a gas, producing a plasma along the substrate's surface. As such, the germicidal lamps which may be considered for the methods and systems described herein include gas-discharge lamps as well as surface-discharge lamps. Discharge lamps may be further characterized by the type of gas/es employed and the pressure at which they are operated. The discharge lamps which may be considered for the methods and systems described herein include those of low pressure, medium pressure and high intensity. In addition, the gas/es employed may include helium, neon, argon, krypton, xenon, nitrogen, oxygen, hydrogen, water vapor, carbon dioxide, mercury vapor, sodium vapor and any combination thereof. In addition, the germicidal light sources considered for the methods and systems described herein may include those which generate continuous light and/or those which generate light in recurrent short durations, the latter of which are referred to herein as pulsed light sources. Discharge lamps which produce recurrent pulses of light are often referred to as flashtubes or flashlamps.

A commonly used gas-discharge lamp used to produce continuous light is a mercury-vapor lamp, which may be considered for some of the methods and systems described herein. It emits a strong peak of light at 253.7 nm, which is considered particularly applicable for germicidal disinfection and, thus, is commonly referenced for ultraviolet germicidal irradiation (UVGI). A commonly used flashlamp which may be considered for the methods and systems described herein is a xenon flashtube. In contrast to a mercury-vapor lamp, a xenon flashtube generates a broad spectrum of light from ultraviolet to infrared and, thus, provides ultraviolet light in the entire spectrum known to the germicidal (i.e., between approximately 200 nm and approximately 320 nm). In addition, a xenon flashtube can provide relatively sufficient intensity in the spectrum which is known to be optimally germicidal (i.e., between approximately 260 nm and approximately 265 nm). Moreover, a xenon flashtube generates an extreme amount of heat, which can further contribute to the deactivation and killing of microorganisms.

Although they are not readily available on the commercial market to date, a surface-discharge lamp may be considered for some of the methods and systems described herein as noted above. Similar to a xenon flashtube, a surface-discharge lamp produces ultraviolet light in the entire spectrum known to the germicidal (i.e., between approximately 200 nm and approximately 320 nm). In contrast, however, surface-discharge lamps operate at higher energy levels per pulse and, thus, greater UV efficiency, as well as offer longer lamp life as compared to xenon flashtubes. It is noted that the aforementioned descriptions and comparisons of a mercury-vapor lamp, a xenon flashlamp, and a surface discharge lamp in no way restrict the methods and systems described herein to include such lamps. Rather, the aforementioned descriptions and comparisons are merely provided to offer factors which one skilled in the art may contemplate when selecting a germicidal light source for methods and systems described herein.

As noted above, in some cases, the germicidal light source may be an excimer laser and, thus, the germicidal light used to disinfect PPE and/or clothing of an individual may be a narrow beam of light set to disinfect a specific location on the PPE and/or clothing. In such cases, a disinfection apparatus comprising the laser may be configured to move the laser such that multiple or all locations on the PPE and/or clothing are disinfected. Alternatively, a disinfection apparatus may be configured to distribute germicidal light into an ambient of a room in a spacious manner such that at least the portions of an individual in the vicinity of the disinfection apparatus may be simultaneously disinfected. The disinfection apparatus may be of any shape, size, or configuration in which to achieve such an objective.

In some cases, a disinfection apparatus may be configured to only disperse light in the general direction of an individual (such as within a few feet on either side of a target location/area for an individual to be situated). In other embodiments, however, the disinfection apparatus may be configured to disperse a wider span of light and, in some cases, may be configured to distribute germicidal light to a continuous ring region around the apparatus. In particular, an apparatus may in some cases be void of an opaque component 360° around an elongated portion of the germicidal light source such that light emitted from the germicidal light source encircles the apparatus. Wider spans of light may be advantageous for embodiments in which reflector walls or panels are arranged behind the disinfection apparatus (i.e., the side of the disinfection apparatus not facing the individual being exposed to the germicidal light) as described in more detail below. Alternatively, wider spans of light may be advantageous for disinfecting multiple individuals during the same disinfection process. In particular, a disinfection apparatus that disperses a relatively wide span of germicidal light could be used for a pre-doffing disinfection process of multiple individuals that area spaced apart and are in light of sight of the light source/s of the disinfection apparatus.

In any case, the disinfection apparatus used in the methods and systems described herein may generally include one or more germicidal light sources, depending on the design specifications of the apparatus. As noted above, terms "germicidal light source" and "germicidal lamp" are used interchangeably herein and refer to a collection of one or more components used to generate and disperse germicidal light. In some cases, a disinfection apparatus may include components in addition to a light source to effect the generation or dispersal of the germicidal light from the light source, such as reflectors, particularly which exhibit a relatively high degree of reflectivity (e.g., greater than approximately 85%). Regardless of the number of germicidal light sources comprising a disinfection apparatus or whether it is equipped with additional components to aid in the dispersal of the germicidal light, the disinfection apparatuses described herein may include other germicidal means, such as but not limited to chemical sprays, fogs or vapors, to aid in the pre-doffing disinfection process.

In some cases, it may be advantageous for the methods and systems disclosed herein to utilize disinfection apparatuses which are configured to direct germicidal light to a region approximately 2 feet and approximately 4 feet from a floor of a room in which the apparatus is arranged. In particular, such a configuration may be advantageous since the noted region will generally contain a mid-portion of an individual. In addition, the region between approximately 2 feet and approximately 4 feet from a floor of a room is considered a "high touch" region of a room since objects of frequent use are generally placed in such a region. Thus, a disinfection apparatus configured to direct light to such a region may be suited for room disinfection processes in addition to pre-doffing processes, which would be advantageous for environments in which both types processes are employed, such as in a hospital for example.

Examples of disinfection apparatuses configured to direct germicidal light to a region approximately 2 feet and approximately 4 feet from a floor of a room in which the apparatus is arranged are disclosed in U.S. application Ser. No. 13/706,926 filed Dec. 6, 2012 and Ser. No. 13/708,208 filed Dec. 7, 2012 as well as International Application No. PCT/US2014/059698 filed Oct. 8, 2014, all of which are incorporated herein by reference as if set forth fully herein. It is noted that a feature which often is in included in apparatuses configured for room disinfection and having UV light sources is an occupancy sensor, particularly such that the generation of UV light may be inhibited and/or terminated upon making a detection which is indicative of occupancy within the area/room in which the apparatus is arranged. In order to accommodate a disinfection apparatus for both room disinfection processes and pre-doffing processes, the disinfection apparatuses considered herein may in some embodiments include a switch to activate and deactivate an occupancy sensor.

In yet other embodiments, an occupancy sensor of a disinfection apparatus may be used in a different manner for a pre-doffing process as compared to a room disinfection process. In particular and as set forth in more detail below, the systems described herein may, in some embodiments, include one or more sensors for detecting an individual in a room in which the disinfection apparatus, particularly within a target area a set distance from the disinfection apparatus and upon detection, activating the disinfection apparatus to generate and project germicidal light and/or move itself within the room to affect a specified distance from the individual donned in potentially contaminated PPE and/or clothing. In yet further embodiments, the disinfection apparatus may be additionally or alternatively configured to determine and/or alter its operational parameters based on a determined location/distance of the individual relative to the disinfection apparatus.

Further to utilizing disinfection sources which are configured to direct germicidal light to a region approximately 2 feet and approximately 4 feet from a floor of a room in which the apparatus is arranged, it may be advantageous in some embodiments to employ a disinfection apparatus in a position such that the germicidal lamp is arranged at an elevation approximately 2 feet and approximately 4 feet from a floor of a room in which the apparatus is arranged. In doing so, the germicidal efficacy of a pre-doffing process may be relatively consistent across a greater vertical portion of an individual (i.e., at least the side of an individual facing the disinfection apparatus) than if a germicidal lamp is positioned below or above such an elevation range. In particular, germicidal efficacy generally decreases with distance and, thus, for example, if a germicidal light source is arranged at an elevation above or below an individual, germicidal efficacy of the light generated therefrom will vary more across a vertical portion of an individual.

In some cases, it may be advantageous for the methods and systems disclosed herein to utilize disinfection apparatuses which are configured to disperse germicidal light across a particular vertical region. For example, it may be advantageous for the methods and systems disclosed herein to utilize disinfection apparatuses which are configured to disperse germicidal light between approximately 2 feet and approximately 4 feet from a floor of a room in which the apparatus is arranged. In some cases, a disinfection apparatus may be configured to disperse germicidal light to a greater vertical range, such as from the floor to approximately 4 feet above the floor or from the floor to at least approximately 7 feet above the floor (the latter of which would be particularly beneficial for disinfecting a size of an individual from head to toe). In some cases, the size and shape of the germicidal light source as well as its arrangement within the disinfection apparatus may constitute a particular vertical range of germicidal light dispersal within a room. For example, a germicidal light source arranged lengthwise substantially perpendicular to a horizontal plane of the apparatus may aid in achieving a particular vertical range of germicidal light dispersal within a room, depending on its length and its placement within the disinfection apparatus. In other embodiments, however, additional provisions may be employed to aid in achieving a desired vertical dispersal of light within a room. For example, reflectors may be used to aid in achieving greater vertical dispersal of germicidal light. Furthermore, some of disinfection apparatuses described herein may include an actuator for moving its germicidal light source within the apparatus (such as with respect to a support structure supporting the light source) to aid in the vertical distribution of light.

Figure 2:
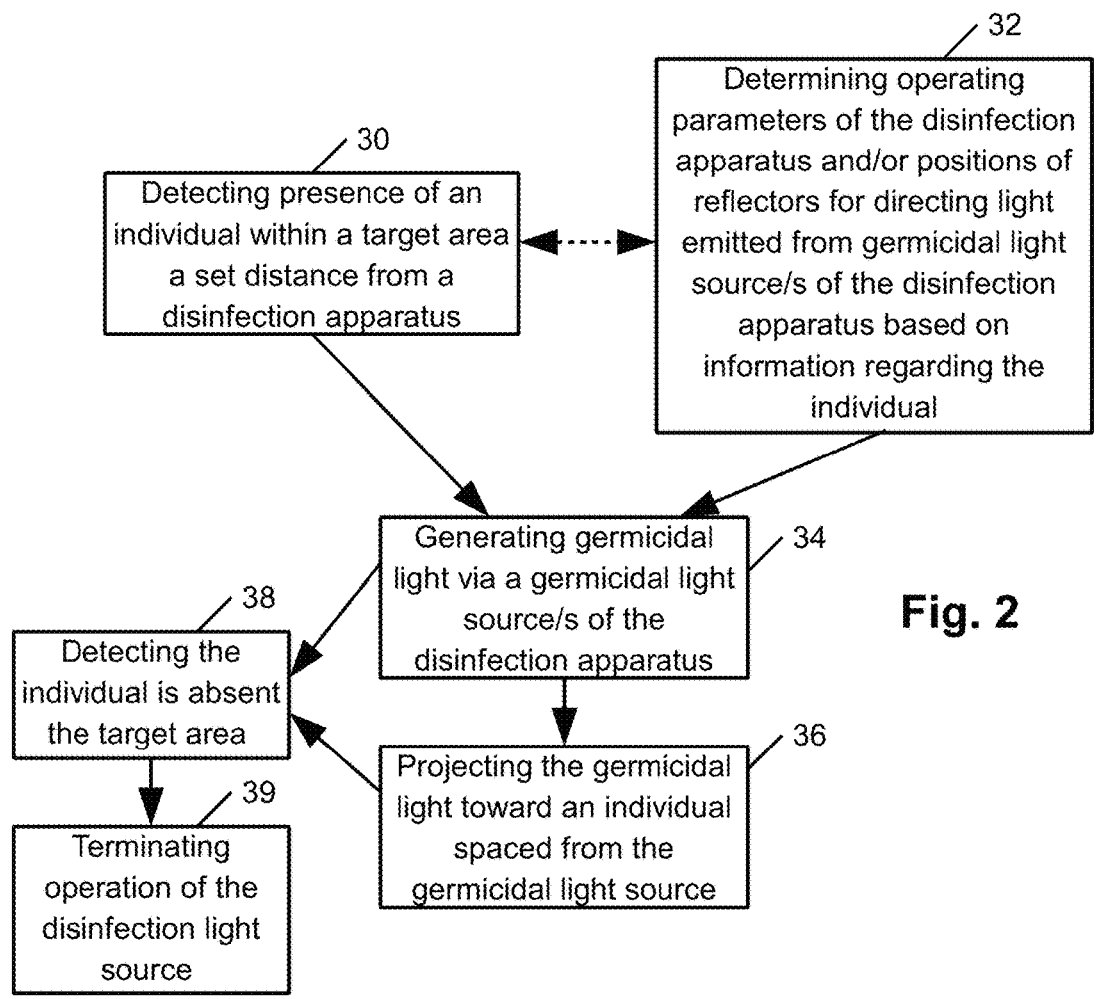
FIG. 2 illustrates an example flowchart of processes that may be conducted by the system depicted in FIG. 1.
Figure 3:
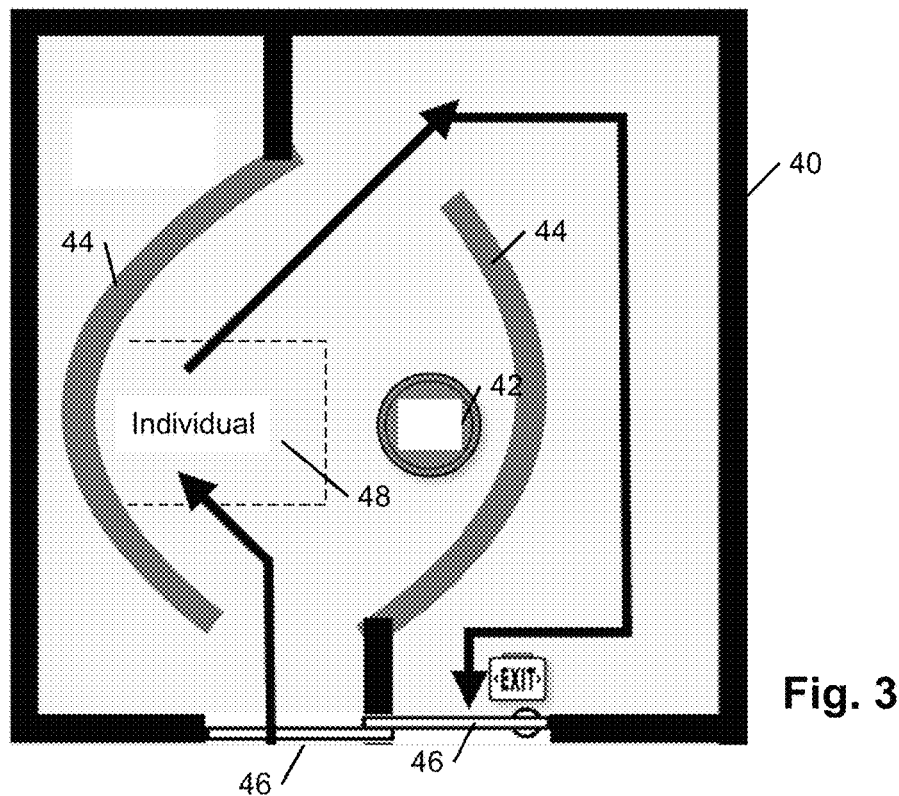
FIG. 3 illustrates an example of a room layout for performing a pre-doffing disinfection process.
Figure 4:
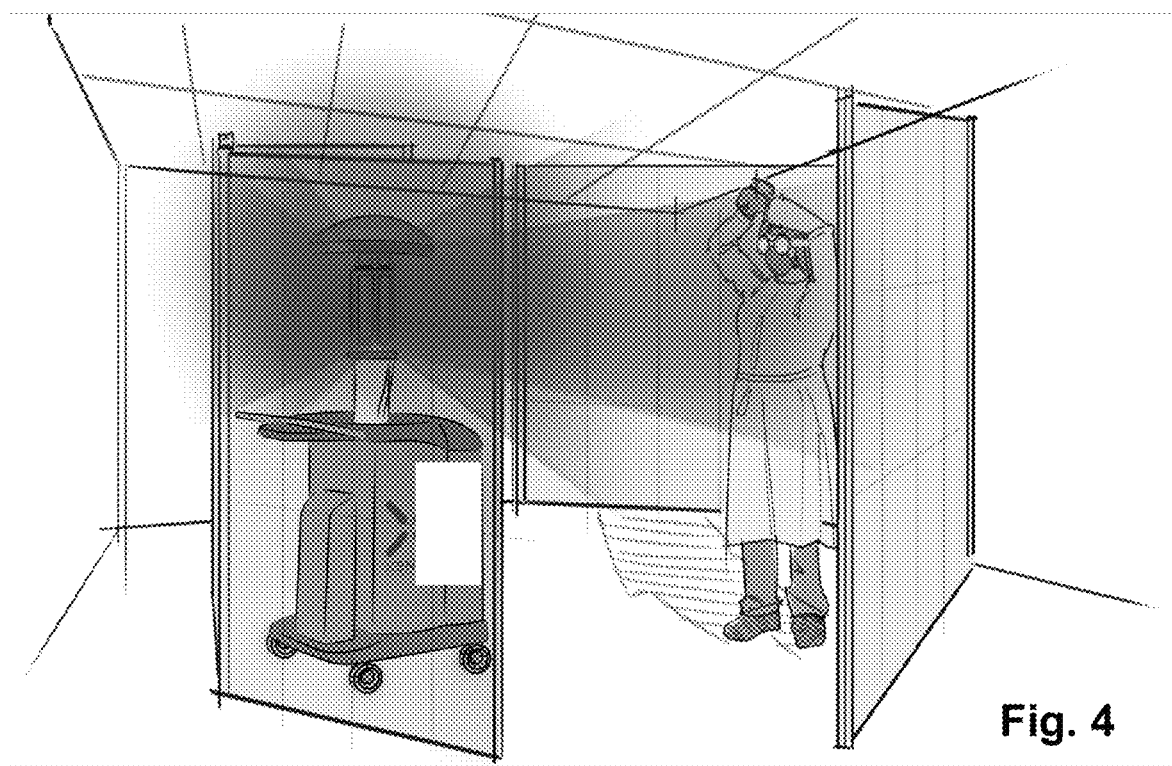
FIG. 4 illustrates an example of a pre-doffing system being used by an individual.
Figure 5:
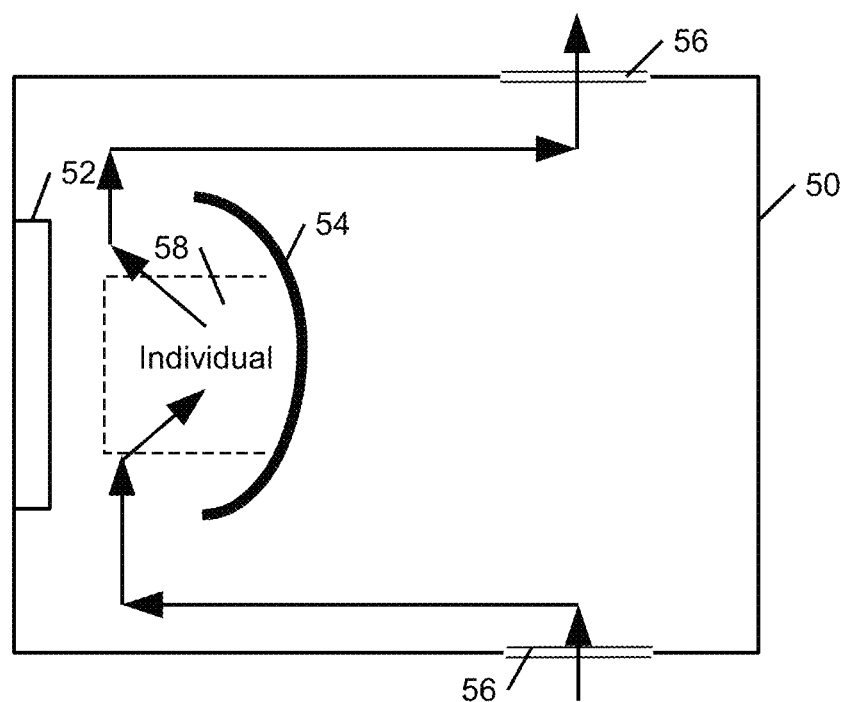
FIG. 5 illustrates another example of a room layout for performing a pre-doffing process.

Turning to the drawings, FIG. 1 illustrates a schematic diagram of an example system for performing a pre-doffing disinfection process, particularly system 10 include disinfection apparatus 12 with one or more germicidal light sources, reflector panels 14, sensors 16, remote user interface 29 and storage medium 20 having components for controlling the operation of disinfection apparatus 12. In addition, FIG. 2 illustrates an example flowchart of processes that may be conducted by the system depicted in FIG. 1. Moreover, FIGS. 3-5 illustrate an example of a room layouts and areas for performing a pre-doffing disinfection process. As will be set forth in more detail below, the systems and methods described herein are not limited to the depictions in the drawings. Several other configurations of systems and methods may be considered. Furthermore, it is noted that the drawings are not necessarily drawn to scale.

In general, disinfection apparatus 12 of system 10 depicted in FIG. 1 may include any of the configurations noted above to the disinfection apparatuses considered herein. Although system 10 is shown having reflector panels 14, sensors 16, remote user interface 29 and storage medium 20, any one or more of such components is optional for system 10. In particular, disinfection apparatus 12 may alone be employed for a pre-doffing process of an individual. In particular, disinfection apparatus 12 may include a power switch which an individual donned in PPE and/or clothing may activate to start the generation and distribution of germicidal light from the disinfection apparatus. As set forth in more detail below, however, reflector panels 14, sensors 16, remote user interface 29 and storage medium 20 may individually or collectively aid in enhancing the functionality and/or efficacy of system 10 and, thus, one or more of such components may be included in system 10.

For example, remote user interface 29 may enable the generation and distribution of germicidal light by the disinfection apparatus to be activated away from disinfection apparatus 12 such that the distance traveled and/or the activities required by the individual donned in potentially contaminated PPE and/or clothing may be minimized. In particular, remote user interface 29 may, in some embodiments, be a remote control device which may be used to activate disinfection apparatus 12 outside of the room in which the apparatus is arranged. In such cases, a person other than the individual donned in potentially contaminated PPE and/or clothing may activate disinfection apparatus 12. In yet other embodiments, remote user interface 29 may be a remote control device arranged within the room in which disinfection apparatus 12 is arranged. In such cases, remote user interface 29 may be arranged in a convenient location for an individual donned in PPE and/or clothing to activate the generation and distribution of germicidal light from disinfection apparatus 12. In other embodiments, remote user interface 29 may be arranged in a region of the room which is shielded from light generated by disinfection apparatus 12 and, thus, a person other than the individual donned in potentially contaminated PPE and/or clothing may activate disinfection apparatus 12 via remote user interface 29. As set forth below, remote user interface 29 may be used for other user input and, thus, it is not necessarily limited to activating disinfection apparatus 12. As such, remote user interface 29 may be coupled to disinfection apparatus 12 and/or storage medium 20 (as denoted by the dotted lines in FIG. 1 between such components), depending on the design specification of system 10.

As shown in FIG. 1, storage medium 20 may include processor 22, program instructions 24, user interface 26 and database 28. User interface 26 and database 28 are optional components of storage medium 20 and, thus, may be omitted in some embodiments. In general, processor 22 is electrically coupled to program instructions 24 such that the program instructions may be executed by the processor and storage medium 20 is coupled to disinfection apparatus 12 such that disinfection apparatus 12 may be controlled in accordance with program instructions 24. In some cases, storage medium 20 may be part of disinfection apparatus 12, but in other embodiments storage medium 20 may be remote from disinfection apparatus 12, including outside the room in which disinfection apparatus 12 is arranged. The term "storage medium," as used herein, refers to any electronic medium configured to hold one or more set of program instructions, such as but not limited to a read-only memory, a random access memory, a magnetic or optical disk, or magnetic tape. The term "program instructions," as used herein, refers to commands within software which are configured to perform a particular function, such as but not limited to any of the processes described in reference to FIG. 2. Program instructions 24 may be implemented in any of various ways, including procedure-based techniques, component-based techniques, and/or object-oriented techniques, among others. Program instructions 24 may be transmitted over or on a carrier medium such as a wire, cable, or wireless transmission link.

Alternative to being activated by remote user interface 29 or user interface 26, system 10 may be configured to determine if an individual is located in a target area a set distance from disinfection apparatus 12 to affect the pre-doffing disinfection process. Alternatively, the disinfection apparatus may be configured to move itself within the room to affect a specified distance from the individual donned in potentially contaminated PPE and/or clothing. In yet further embodiments, the disinfection apparatus may be additionally or alternatively configured to determine and/or alter its operational parameters based on information regarding the individual donned in potentially contaminated PPE and/or clothing, such as but not limited the determined location/distance of the individual relative to the disinfection apparatus. In any of such cases, the specified distance between the disinfection apparatus and the individual may be any distance which does not compromise of the safety integrity of the contaminated PPE and/or clothing worn by the individual in the pre-doffing process. In particular, many types of germicidal light sources generate intense amounts of heat and, thus, pose a risk of causing items too close to the bulb to melt or catch fire. In addition, in embodiments in which disinfection apparatus includes a UV light source, UV permeability through PPE and/or clothing may be a concern if they are in close proximity to the bulb. Furthermore, the set distance may be any distance which is believed to affect sufficient germicidal efficacy for the pre-doffing process. An exemplary range of set distances considered for the pre-doffing processes described herein is between approximately 1 foot and approximately 3 meters, but shorter and longer distances may be employed.

In any case, the configuration of system 10 to affect detection of an individual in a room may be via sensor/s 16 and sensor/s 16 may include one or more of any device known to affect detection. For example, sensor/s 16 may include a proximity sensor, a motion detection sensor and/or a photo recognition device. In some cases, one or more of sensor/s 16 may be disposed on or within a support structure of disinfection apparatus 12. In addition or alternatively, sensor/s 16 may be separate from disinfection apparatus 12 but are in communication with disinfection apparatus 12. For example, in some cases, a weight sensor may be placed within a floor of a room at a location in which an individual is to position themselves for the disinfection process or within a platform on which an individual is to position themselves for the disinfection process. In such embodiments, the weight sensor may be in communication with the disinfection apparatus to start the generation and distribution of germicidal light and/or determine and/or alter parameters of the disinfection apparatus.

As described above, the systems and methods described herein may include reflectors for directing light to an individual donned in potentially contaminated PPE and/or clothing, particularly but not limited to optimizing the vertical range of the light dispersal from the disinfection apparatus.

More specifically, the systems and methods described herein may include devices having at least a portion of it which is highly reflective to germicidal light, particularly ultraviolet light and/or visible violet-blue light. In particular, it may be advantageous for at least a portion of the devices to include a material which exhibits greater than 50% reflectance, or more specifically, greater than 85% reflectance. Examples of reflective materials which may be employed include but are not limited to metalized nylon, Teflon, aluminum, reflective paint, biaxially-oriented polyethylene terephthalate (boPET) (e.g., Mylar), and GORE® DRP® Diffuse Reflector Material available from W. L. Gore & Associates, Inc. In addition or alternative to being highly reflective, the devices may include a variety of other material characteristics (particularly on the side facing the disinfection apparatus), such as but not limited to being antimicrobial and/or fire resistant.

In some embodiments, the reflectors may be incorporated within the disinfection apparatus. In addition or alternatively, reflectors independent of the disinfection apparatus may be used in the methods and systems described herein. For example, the systems and methods described herein may include reflective walls or panels as shown for system 10 of FIG. 1. In general, the reflective walls or panels may be arranged at least partially surrounding the disinfection apparatus and/or the region at which the individual donned in potentially contaminated PPE and/or clothing is situated during the disinfection process. Examples of possible arrangements of reflective walls or panels for a pre-doffing process are shown in FIGS. 3-5 and described in more detail below. Any number and arrangement of walls or panels may be used for the systems and methods described herein and, thus, the systems and methods should not be limited to the depictions of FIGS. 3-5.

In some cases, reflective walls or panels may be arranged to provide for disinfection on all sides of the individual donned in potentially contaminated PPE and/or clothing and/or assure that the germicidal light reaches the full body of the person (assuming a max height of approximately 7 feet). More specifically, reflective walls or panels may be arranged to disperse the germicidal light to provide coverage from the floor to at least approximately seven feet and, in some cases, on all sides of the individual standing in a designated area. In other words, the reflectors would be designed to optimize the germicidal light dose on a person standing a set distance from the germicidal light source (less than 3 kmeters) for a set amount of (such as 5 minutes or less). Such an arrangement may allow the individual to stay in one place during disinfection process without having to turn around. Furthermore, this arrangement would allow for thorough and reliable disinfection of the PPE and/or clothing while shortening the time of the disinfection process, particularly less than 5 minutes in some cases.

In some cases, the methods and systems described herein may be configured to determine operating parameters of the disinfection apparatus and/or positions of the one or more reflectors based on information regarding an individual who is in the presence of the disinfection apparatus or who is scheduled to be in the presence of the disinfection apparatus. In some cases, the information may be a position of the individual relative to the disinfection apparatus as described above in regard to sensor/s 16. In other cases, the information may additionally or alternatively be a target microorganism suspected of contaminating the PPE or clothing worn by the individual. In yet other embodiments, the information may additionally or alternatively be size information of the individual, such as but not limited to the height of the individual. As used herein, "operating parameters of the disinfection apparatus" refers to any parameter which may affect operation of a disinfection apparatus, including but not limited to run time of a disinfection apparatus, position of a disinfection apparatus, orientation of components comprising a disinfection apparatus, germicidal dosing parameters for the disinfection apparatus, and/or power supplied to a disinfection apparatus. In cases in which the disinfection apparatus includes a pulsed germicidal light source, such as a flashlamp for example, germicidal dosing parameters for the disinfection apparatus may include pulse duration and/or pulse frequency of the germicidal light source. Furthermore, in embodiments in which the germicidal light source is a flashlamp, power supplied to the flashlamp may be referred to as "pulse intensity" or "intensity of the lamp".

In some cases, the systems described herein may include a database and program instructions for retrieving size information from the database in response to receiving input regarding an identity of the individual. In addition or alternatively, size or microorganism information regarding the individual may be input into a user input interface (either a remote or not remote interface) of the system to affect the determination of operating parameters of the disinfection apparatus and/or the positions of one or more reflectors. In yet other cases, the systems described herein may additionally or alternatively include one or more sensors for determining size information and/or one or more sensors for determining a position of the individual relative to the disinfection apparatus and such information may be retrieved from the sensors to affect the determination of operating parameters of the disinfection apparatus and/or the positions of one or more reflectors. Any of the sensor types described above in reference to sensor/s 16 may be used for determining size information or position of an individual and are not reiterated for the sake of brevity. Furthermore, the depiction of sensor/s 16 in system 10 of FIG. 1 may refer to sensors for either or both functionality.

In some cases, the systems described herein may be configured to automatically move the reflectors of the system and/or automatically alter the operating parameters of the disinfection apparatus based on information regarding the individual who is in the presence of the disinfection apparatus or who is scheduled to be in the presence of the disinfection apparatus. In particular, the systems described herein may include program instructions to affect alterations in operating parameters and/or may include actuators for moving reflectors or components of the disinfection apparatus or motorized wheels for moving the disinfection apparatus itself. In some cases, it may be advantageous to limit the time it takes to modify operating parameters and/or positions of reflectors while an individual is in the presence of the disinfection apparatus and, thus, the set points to activate such modifications may be limited to just a few. For example, the modifications may be activated based on the height of the individual being closest to set points of 4 feet, 5 feet, 6 feet and 7 feet. In other embodiments, set points of greater granularity may be used.

FIG. 2 illustrates an example flowchart of processes that may be conducted by the systems described herein, particularly the processes described above in regard to FIG. 1. In particular, as noted in block 30 of FIG. 2, the systems and methods described herein may include detecting the presence of an individual within a target area a set distance from a disinfection apparatus. In addition or alternatively, the systems and methods described herein may include determining operating parameters of the disinfection apparatus and/or positions of the one or more reflective panels based on information regarding an individual who is in the presence of the disinfection apparatus or who is scheduled to be in the presence of the disinfection apparatus as denoted in block 32. In some cases, the processes of blocks 30 and 32 may be both performed for a pre-doffing process. In such embodiments, the processes of blocks 30 and 32 may be performed simultaneously or one after the other in either order. In any case, the results of either or both blocks may cause the disinfection apparatus to generate and project germicidal light toward an individual spaced from the disinfection apparatus as denoted in blocks 34 and 38. In some cases, the systems and methods described herein may include monitoring and detecting whether an individual is absent the target area or moves out of the target area as denoted in block 38. In addition or alternatively, the systems and methods described herein may include detecting whether the individual comes within a predetermined safety threshold distance from the germicidal light source of the disinfection apparatus. Upon detection of any of such scenarios, the systems and methods described herein may include terminating operation of the disinfection light source.

In any case, the systems described herein may, in some embodiments, be configured to project audio commands (i.e., have a speaker and program instructions for sending signals for an audio command to be broadcasted) and/or display visual commands (i.e., include as screen and program instructions for displaying text or pictorial information thereon) to instruct an individual to position themselves to a target location within the room prior to disinfection apparatus generating and distributing germicidal light. In addition or alternatively, the systems described herein may be configured to instruct an individual (via audio or visual commands) when and/or in which direction to go after a disinfection process is complete. In some cases, the systems described herein may be configured to instruct an individual (via audio or visual commands) to make movements during a disinfection process, such as but not limited to turning their entire body around, lifting and/or turning arms and/or hands, spreading fingers, etc. For example, the systems described herein may be configured to instruct an individual to turn around at a mid-point of the disinfection process (e.g., 2.5 minutes into a disinfection cycle). In yet other embodiments, the individual need not move during the disinfection process.

In some embodiments, a pre-doffing process may include an individual, while wearing PPE and/or other types of outerwear and/or clothing, entering into an area or space designated for germicidal light disinfection. In general, the area or space in which the individual enters to have their PPE and/or clothing disinfected by germicidal light may be a room, a portion of a room or an enclosed space suitable for human occupancy having a separate entrance and exit. The phrase "suitable for human occupancy" as used herein refers to a space in which an adult human being of average size may comfortably occupy for at least a period of time to eat, sleep, work, lounge, partake in an activity, or complete a task therein. Examples of spaces which are suitable for human occupancy include but are not limited to single patient rooms, multiple occupancy patient rooms, bathrooms, walk-in closets, hallways, bedrooms, offices, operating rooms, patient examination rooms, waiting and/or lounging areas and nursing stations. In some cases, spaces suitable for human occupancy may be a room in that they are bounded and include at least one door for entering and exiting the room. In other cases, a space suitable for human occupancy may be an area with indeterminate boundaries. As used herein, the term "enclosed space" refers to an area having its boundaries defined by barriers blocking a vast majority or all germicidal light transmission exterior to the area.

FIG. 3 illustrates an example of a room that may be used for a predoffing process. In particular, FIG. 3 shows room 40 with disinfection apparatus 42 disposed within an area partially surrounded by reflector walls/panels 44. As further shown in FIG. 3, room 40 includes dual sliding doors 46, one designated for entrance into the room and the other for the exit to the room. Other configurations of separate entrance/exit, however, can be employed. In any case, as shown in FIG. 3, the room may be clearly labeled with a pathway for an individual to follow for the pre-doffing process, specifically such that the individual does not backtrack but rather leave the area via the exit versus the entrance. In doing so, recontamination of the individual's PPE and/or clothing may be prevented. An example of labeling a pathway is to put arrows and/or lines on a floor of a room or enclosed space to signify a footpath to follow. Other types of labeling, however, may be used. In some cases, the spot/area at which an individual can be situated for the pre-doffing process may be labeled.

FIG. 3 illustrates an example configuration of reflector walls/panels 44 forming a subsection of the room in which disinfection apparatus 42 may be arranged and further includes area 48 in which an individual may be situated to expose their potentially contaminated PPE and/or clothing to germicidal light. Reflector walls/panels 44 are shown partially surrounding disinfection apparatus 42 and area 48, particularly leaving openings for entering and exiting the region. FIG. 4 illustrates an example of a pre-doffing system having a similar sectioned off area in use. Other configurations of walls and reflectors, however, may be used. For example, the reflector walls/panels may be connected to doors for entering and exiting the region, and, thus, the reflector walls/panels with the doors may make up a chamber or enclosed space in of itself. In any case, the arrangement of the walls or panels may be arranged to section a region of any size or shape of a room. As such, the walls or panels need not surround a circular region of a room as shown in FIGS. 3 and 4. In some cases, however, it may be advantageous to arrange the walls or panels to surround a circular region.

In yet other cases, reflector walls/panels 44 may only be arranged proximate one of disinfection apparatus 42 and area 48. In particular, reflector walls/panels proximate area 48 may be advantageous for directing light to a side of an individual not facing disinfection apparatus 42, but such coverage may not be desirable in some situations. In addition, reflector walls/panels proximate disinfection apparatus 42 may be advantageous when the disinfection apparatus disperses a wide span of germicidal light, particularly to focus more of the light toward the individual, but it may not be necessarily prudent in all applications, such as but not limited to when the disinfection apparatus does not have a particularly wide dispersal of germicidal light. In yet other cases, room 40 may not include reflector walls or panels to specifically section off disinfection apparatus 14 and area 16.

In general, any area having a separate entrance and exit can be used to disinfect PPE and/or clothing on an individual by germicidal light. In this regard, the room or area in which a pre-doffing disinfection process is performed may be a room or area permanently designated for such a process and, thus, the disinfection apparatus, labels and/or reflector walls may be fixed components of the room. In other cases, a room or area in which the pre-doffing disinfection process is performed may be a temporary set-up. For example, adjoining patient rooms could be ad hoc for the disinfection process. In such cases, it may be advantageous for the disinfection apparatus, labels, and/or reflector walls to be readily portable. For example, optional features for the disinfection apparatuses may be wheels and/or a handle to affect portability for the apparatuses.

FIG. 5 illustrates an example of a room having a disinfection apparatus fixed therein for a predoffing process. In particular, FIG. 5 shows room 50 with disinfection apparatus 52 fixedly arranged against a wall of the room and configured to project germicidal light toward target area 58 having reflector wall/panel 54 therebehind. Other arrangements of disinfection apparatus 52, target area 58 and reflector wall/panel 54 may be considered and/or reflector wall/panel 54 may be omitted from the room. In any case, as further shown in FIG. 5, room 50 includes doors 56, one designated for entrance into the room and the other for the exit to the room. Other configurations of separate entrance/exit, however, can be employed. In any case, as shown in FIG. 5, room 50 may be clearly labeled with a pathway for an individual to follow for the pre-doffing process, specifically such that the individual does not backtrack but rather leave the area via the exit versus the entrance.

It will be appreciated to those skilled in the art having the benefit of this disclosure that this invention is believed to provide systems and methods which disinfect PPE with germicidal light while it is worn by an individual. Further modifications and alternative embodiments of various aspects of the invention will be apparent to those skilled in the art in view of this description. For example, the methods and systems provided herein are specifically described in reference to pre-doffing processes for individuals covered in PPE and/or clothing such that no skin is exposed, but the methods and systems are not necessarily so restricted. In particular, the methods and systems may be used to for pre-doffing processes in which PPE and/or clothing only partially cover an individual. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims. The term "approximately" as used herein refers to variations of up to +/−5% of the stated number.

What is claimed is:

1. A system, comprising:
    a disinfection apparatus comprising one or more germicidal light sources, wherein the disinfection apparatus is configured such that germicidal light generated from the one or more germicidal light sources is projected at least approximately 1 foot from the disinfection apparatus and at least approximately 7 feet from a floor of an area in which the disinfection apparatus is arranged; and
    a storage medium comprising program instructions executable by a processor for determining one or more operating parameters of the disinfection apparatus based on size information regarding an individual who is in the presence of the disinfection apparatus or who is scheduled to be in the presence of the disinfection apparatus, wherein the one or more operating parameters comprise a run time of the disinfection apparatus, a position of the disinfection apparatuses within the area, an orientation of a component comprising the disinfection apparatus, one or more germicidal dosing parameters for the disinfection apparatus and/or power supplied to the disinfection apparatus.

2. The system of claim 1, wherein the program instructions for determining the one or more operating parameters of the disinfection apparatus are further based on information regarding a target microorganism suspected of contaminating clothing and/or personal protective equipment worn by the individual.

3. The system of claim 1, wherein the program instructions for determining the one or more operating parameters of the disinfection apparatus are further based on information regarding a position of the individual relative to the disinfection apparatus.

4. The system of claim 1, further comprising a database, wherein the program instructions are further for retrieving the size information from the database.

5. The system of claim 1, further comprising one or more sensors for determining the size information, wherein the program instructions are further for retrieving the size information from the one or sensors.

6. The system of claim 1, further comprising a user input interface, and wherein the program instructions are further for receiving the size information from the user input interface.

7. The system of claim 1, further comprising one or more reflective panels exhibiting greater than approximately 85% reflectance, wherein the storage medium further comprises program instructions executable by a processor for determining positions of the one or more reflector panels based on information regarding the individual.

8. A system, comprising:
    a disinfection apparatus comprising one or more germicidal light sources; and
    one or more reflective panels exhibiting greater than approximately 85% reflectance to germicidal light, wherein the one or more reflective panels are arranged to direct light projected from the disinfection apparatus to a target area which is spaced at least approximately 1 foot from the disinfection apparatus and extends at least approximately 7 feet from a floor of a room in the target area;
    a storage medium comprising program instructions executable by a processor for determining one or more operating parameters of the disinfection apparatus based on size information regarding an individual who is in the presence of the disinfection apparatus or who is scheduled to be in the presence of the disinfection apparatus.

9. The system of claim 8, wherein the one or more operating parameters comprise a run time of the disinfection apparatus, a position of the disinfection apparatus within the area, an orientation of a component comprising the disinfection apparatus, one or more germicidal dosing parameters for the disinfection apparatus and/or power supplied to the disinfection apparatus.

10. The system of claim 8, wherein the program instructions for determining the one or more operating parameters of the disinfection apparatus are further based on information regarding a target microorganism suspected of contaminating clothing and/or personal protective equipment worn by the individual.

11. The system of claim 8, wherein the program instructions for determining the one or more operating parameters of the disinfection apparatus are further based on information regarding a position of the individual relative to the disinfection apparatus.

12. A system, comprising:
- a disinfection apparatus comprising one or more germicidal light sources; and
- a storage medium comprising program instructions executable by a processor for determining a position of the disinfection apparatus in a room/area based on size information regarding an individual who is in the presence of the disinfection apparatus or who is scheduled to be in the presence of the disinfection apparatus.

13. The system of claim 12, wherein the storage medium further comprises program instructions executable by a processor for determining one or more additional operating parameters of the disinfection apparatus based on information regarding the individual.

14. The system of claim 13, wherein the one or more additional operating parameters comprise a run time of the disinfection apparatus, an orientation of a component comprising the disinfection apparatus, one or more germicidal dosing parameters for the disinfection apparatus and/or power supplied to the disinfection apparatus.

15. The system of claim 12, wherein the program instructions for determining a position of the disinfection apparatus in a room/area are further based on information regarding a target microorganism suspected of contaminating clothing and/or personal protective equipment worn by the individual.

16. The system of claim 12, wherein the program instructions for determining a position of the disinfection apparatus in a room/area are further based on information regarding a position of the individual relative to the disinfection apparatus.

17. The system of claim 12, wherein the size information is height of the individual.

18. The system of claim 12, further comprising one or more reflective panels exhibiting greater than approximately 85% reflectance, wherein the storage medium further comprises program instructions executable by a processor for determining positions of the one or more reflector panels based on information regarding the individual.

* * * * *